United States Patent [19]

Kende et al.

[11] Patent Number: 4,902,835

[45] Date of Patent: Feb. 20, 1990

[54] FLUORINATED BUTENE DERIVATIVES AND METHODS FOR THEIR PREPARATION

[75] Inventors: Andrew S. Kende, Rochester, N.Y.; Noritada Matsuo, Minamino, Japan

[73] Assignee: The University of Rochester, Rochester, N.Y.

[21] Appl. No.: 142,630

[22] Filed: Jan. 11, 1988

[51] Int. Cl.$^4$ .................... C07C 41/05; C07C 43/15; C07C 43/166

[52] U.S. Cl. .................... 568/684; 568/661; 568/663; 568/683; 568/685; 568/58; 568/35; 568/32; 560/219; 564/226; 520/136

[58] Field of Search ............... 568/661, 663, 683, 684, 568/685

[56] References Cited

PUBLICATIONS

Matsuo et al, J. Org. Chem 1980, 53, 2324–2328.
R. Filler, Chemtech (1974), 752.
P. Tarrant et al, Org. Chem (1963) 28, 839.
E. D. Bergmann et al., J. Chem. Soc. (C) (1968), 1232.
V. Dedek et al., Coll. Czechoslou Chem Commun, 44, 2260 (1979).
T. Kitazume et al, Chemistry Lett. (1981) 1259.
AR-4 Park et al J.A.C.S. (1956) vol. 78, 859 (cited p. 9).
AR-5 Synth. Comm. (1985) 15, 819 (cited p. 13).
Y. Kobayashi et al, Tetrahedron Lett (1981) 22, 5297.
L. Blanco et al, Bull. Soc. Chim. FR. (1985), 3, 455.
Y. Nakayama et al, J. Flourine Chem (1985), 29, 445.

*Primary Examiner*—Howard T. Mars
*Attorney, Agent, or Firm*—Martin Lukacher

[57] ABSTRACT

New chemical reactions of 1,1,2-trifluoro-1,3-butadiene provide simple access to a series of new fluorinated alkene derivatives. These derivatives provide a simple, general methodology for the stereocontrolled preparation of 2-fluoro-2-alkenoate esters and related monofluoroalkene derivatives which include fluoro analogs of known insecticides, pheromones or pharmaceuticals. A new method for the preparation of 1,1,2-trifluoro-1,3-butadiene is also provided.

4 Claims, No Drawings

FLUORINATED BUTENE DERIVATIVES AND METHODS FOR THEIR PREPARATION

FIELD OF THE INVENTION

This invention relates to a series of new fluorinated alkene derivatives and methods for their preparation.

BACKGROUND OF THE INVENTION

In the field of synthetic organic chemistry there is great interest in the synthesis of fluoro analogs of known biologically active compounds, such as insecticides, pheromones or pharmaceuticals. As described by R. Filler, *Chemtech* 1974, 752, fluorine as a substituent most closely resembles hydrogen with respect to steric requirements at enzyme receptor sites. However, because of its high electro-negativity, fluorine substitution alters the electronic behavior of the compound. Since the carbon-fluorine bond energy is very high, the fluorine substituent imparts increased oxidative and thermal stability. Fluorine substitution also leads to increased lipid solubility in membranes, thus enhancing the rates of absorption and transport of the compound. Thus fluoro compounds often show similar types of biological activity to their hydrogen analogs but modified by differences in absorption, transport and metabolic rates. As indicated in the above reference, in the pharmaceutical field fluorine substitution has provided compounds of great importance in cancer treatment as well as anesthetics, tranquilizers, adrenocortical and anti-inflammatory drugs, progestational agents and drugs for androgenic hormone therapy.

In the synthetic pathways to fluoro analogs of known biologically active compounds (Z)-2-fluoro-2-alkenoate esters and their derivatives provide valuable intermediates. Syntheses of these esters are described in the following chemical journal articles: Machleidt, H.; Wessendorf, R. *Liebigs Ann.* 1964, 674, 1. Tarrant, P.; Johncock, P.; Savory, J. *J. Org. Chem.* 1963, 28, 839; Bergmann, E. D.; Shahak, I.; Sali, E.; Aizenshtat, Z. *J. Chem. Soc. C* 1968, 1232; Dedek, V.; Kovak, M. *Coll. Czechoslov. Chem. Commun.* 1979, 44, 2660; Kitazume, T.; Ishikawa, N. *Chemistry Lett.* 1981, 1259; Kobayashi, Y.; Morikawa, T.; Yoshizawa, A.; Taguchi, T. *Tetrahedron Lett.* 1981, 22, 5297; Blanco, L.; Rousseau, G. *Bull. Soc. Chim. Fr.* 1985, 3, 455; and Nakayama, Y.; Kitazume, T.; Ishikawa, N. *J. Fluorine Chem.* 1985, 29, 445. However, existing methods for the preparation of 2-fluoro--alkenoate esters have the disadvantages of complexity and high cost. Moreover, most of these methods yield mixtures of the two geometric stereoisomers which are possible about the double bond of the alkene chain. For biological purposes it is desirable to produce a single preferred stereoisomer.

SUMMARY OF THE INVENTION

In accordance with the invention, there are provided a series of new fluorinated alkene derivatives and methods for their preparation which are simple, economical and stereospecific. The new fluorinated compounds of the invention are useful as intermediates in the preparation of biologically active compounds which are fluoro analogs of known insecticides, pheromones and pharmaceuticals.

DETAILED DESCRIPTION OF THE INVENTION

The compounds of the invention are fluorinated alkene compounds of the formula selected from the group consisting of

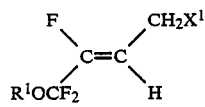  I.

wherein $R^1$ is $C_1$–$C_4$ alkyl; $X^1$ is $C_1$–$C_8$ alkyl; $C_2$–$C_8$ alkenyl, $C_2$–$C_8$ alkynyl, aryl such as phenyl, tolyl, 1-naphthyl and 2-naphthyl, aralkyl such as benzyl or phenethyl, chlorine or bromine;

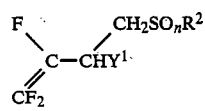  II.

wherein $Y^1$ is chlorine or bromine; $R^2$ is lower alkyl, such as $C_1$–$C_6$ alkyl, phenyl or phenyl substituted with e.g. lower alkyl or halogen; n is an integer of from 0 to 2;

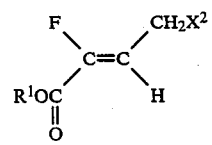  III.

wherein $R^1$ is as described above; $X^2$ is $C_1$–$C_{26}$ alkyl, $C_2$–$C_{26}$ alkenyl, $C_2$–$C_{26}$ alkynyl, aryl such as phenyl, tolyl, 1-naphthyl and 2-naphthyl, aralkyl such as benzyl or phenethyl, $P^+(R^2)_3\ Y^2{}^-$,

or $SO_2R^2$; $Y^2$ is chlorine, bromine or iodine, $R^2$ is as described above;

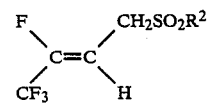  IV.

wherein $R^2$ is as described above;

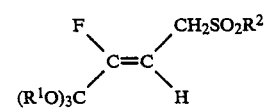  V.

wherein $R^1$ is as described above; $R^2$ is as described above;

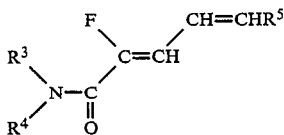

wherein $R^3$ and $R^4$ taken singly are lower alkyl such as $C_1$–$C_6$ alkyl, or taken together can be the carbon atoms necessary to complete a saturated 5 or 6-membered ring; $R^5$ is phenyl or phenyl substituted with lower alkyl such as $C_1$–$C_6$ alkyl, lower alkoxy such as $C_1$–$C_6$ alkoxy, bisalkoxy or methylenedioxy.

Examples of the compounds of the invention are as follows.
Formula I :
 (Z)-4-bromo-1-methoxy-1,1,2-trifluoro-2-butene
Formula II :
 3-chloro-4-phenylthio-1,1,2-trifluoro-1-butene
 3-chloro-4-phenylsulfonyl-1,1,2-trifluoro-1-butene
Formula III:
 (Z)-methyl 2-fluoro-2-decenoate
 (Z)-methyl 2-fluoro-4-phenyl-2-butenoate
 (Z)-methyl 2-fluoro-2-hexenoate
 (Z)-methyl 2-fluoro-4-phenylsulfonyl-2-butenoate
 (Z)-3-fluoro-3-methoxycarbonyl-2-propenytriphenyl-phosphonium bromide
 (Z)-ethyl 2-fluoro-4-(diethylphosphono)-2-butenoate
Formula IV :
 (Z)-3,4,4,4-tetrafluoro-2-butenyl phenylsulfone
Formula V :
 (Z)-3-fluoro-4,4,4-trimethoxy-2-butenyl phenylsulfone
Formula VI :
 (2Z,4E)-2-Fluoro-5-(3,4-methylenedioxyphenyl)-penta-2,4-dienoic acid piperidide The invention provides a process for preparing a diene compound of the formula VII,

     VII an intermediate useful in the preparation of the compounds of the invention, which comprises causing the compound of the formula VIII

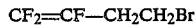     VIII to react with an aqueous alkali metal hydroxide solution in the presence of a phase transfer catalyst. The alkali metal hydroxide is in the range of from 1 to 5 moles per mole of starting material. The phase transfer catalyst includes, for example, benzyl trialkylammonium chlorides or bromides, tetraalkylammonium chlorides or bromides, phenyl trialkylammonium chlorides or bromides, tri(methoxy ethoxyethyl)amine and 18-crown-6. In the reaction, inert solvents such as toluene, xylene and the like may be used. The reaction time is between 5 and 24 hours, generally between 5 to 10 hours. The reaction can be carried out over a wide temperature range, but for optimum reaction rate 50°–70° C. is preferred.

The product is most conveniently collected by sweeping the reaction mixture with a slow stream of inert gas such as nitrogen or argon and cooling the exit gas to about −78° C. to condense the reaction product.

The diene compound can also be prepared by the previously known reaction of 4-iodo-1,1,2-trifluoro-1-butene with aqueous sodium hydroxide, but the yield of the method is only 52% (Park, J. D.; Seffl, R. J.; Lacher, J. R. J.Am. Chem. Soc., 1956, 78, 59).

The invention also provides a process for preparing a masked ester compound of the invention of the formula IX

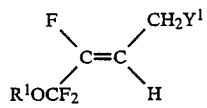     IX wherein $R^1$ and $Y^1$ are as described above, which comprises causing the diene of the formula VII to react with a source of positive chlorine or bromine in a lower alkanol solvent. The positive chlorine or bromine can be provided from free halogen or sources such as N-chloro or N-bromosuccinimide. Examples of the lower alkanol are methanol, ethanol and n-propanol. Preferably the reaction is carried out in the presence of a weak base, such as an alkali metal carbonate or bicarbonate.

For optimum yield and product purity the reaction should be carried out in the temperature range from about −70 to −30° C. Higher temperatures can be used, but with sacrifice of yield and purity.

The masked ester is readily converted to the free ester of formula X

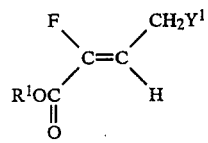     X in the process of the invention by hydrolysis, preferably using a strong aqueous mineral acid such as sulfuric or hydrochloric acid. In its masked form the masked ester is a useful intermediate, allowing reactions such as alkylation or arylation with a Grignard agent to take place on other positions in the molecule without undesired reaction with the ester group itself. The ester group can be readily formed after the alkylation or other desired reaction by treatment with aqueous mineral acid.

The invention also provides a process for preparing a phosphonium compound of the invention of formula XI, wherein $R^1$, $R^2$ and $Y^2$ are as described above,

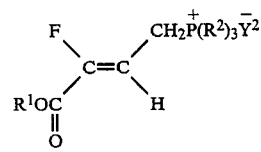     XI by causing the free ester of formula X to react with a triphenyl or tri(lower alkyl) phosphine in an inert solvent such as toluene or xylene, preferably in the temperature range of 40° to 110° C.

The invention also provides a process for preparing a compound of the invention of the formula XII

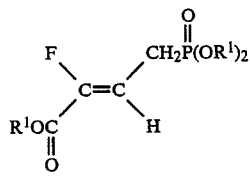

XII wherein $R^1$ is as described above, wherein the free ester of formula X is caused to react with a trimethyl or triethyl phosphite. A solvent is not required.

The invention additionally provides a process for preparing an ester of the formula XIII

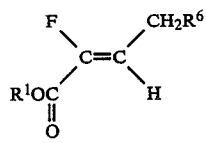

XIII wherein $R^1$ is as described above and $R^6$ is $C_1$–$C_{26}$ alkyl, $C_2$–$C_{26}$ alkenyl, $C_2$–$C_{26}$ alkynyl, aryl such as phenyl, p-tolyl or 2-naphthyl, or aralkyl such as benzyl or phenethyl, which comprises causing a masked ester of the invention of formula IX to react with an organometallic reagent of the type $R^6MgY^2$ or $(R^6)_2CuLi$, wherein $Y^2$ is chlorine, bromine or iodine, and subjecting the resulting product to acid hydrolysis. When a Grignard reagent $R^6MgY^2$ is used, it is preferable to carry out the reaction in the presence of a copper-containing catalyst such as copper(I) chloride or copper(II) chloride-lithium chloride (1:2) complex.

The invention also provides a process for preparing a fluorinated alkene according to formula II of the invention, which comprises causing the diene of the formula VII to react with a sulfenyl halide $R^2SY^1$, wherein $R^2$ and $Y^1$ are as described above. Examples of the sulfenyl halide are methyl sulfenyl chloride or phenyl sulfenyl chloride. In the reaction, an inert solvent such as dichloromethane is preferably used.

The compounds and processes of this invention may be used to prepare biologically active compounds which are fluoro analogs of known insecticides, pheromones or pharmaceuticals. For example, the compound XIV below is the fluoro analog of a pheromone and can be synthesized from a compound of formula I of the invention by the sequence shown [cf. Synthetic Communications 15, 819 (1985)].

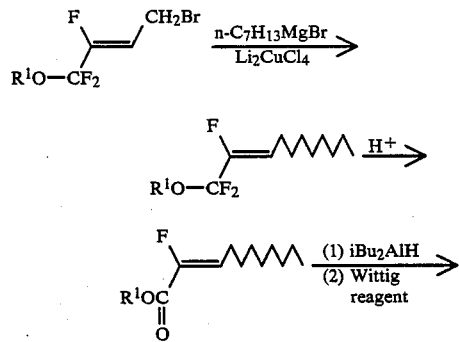

-continued

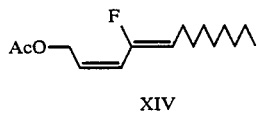

XIV

Similarly, the compound XVI below of formula VI of the invention is the monofluoro analog of the known insecticide piperine. The compound can be prepared from a compound of the invention of the formula XV below by condensation with piperonal, and transformation of the ester to the corresponding amide by the known chemistry:

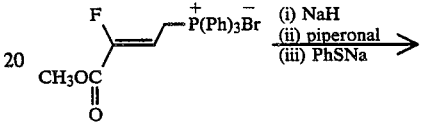

XV

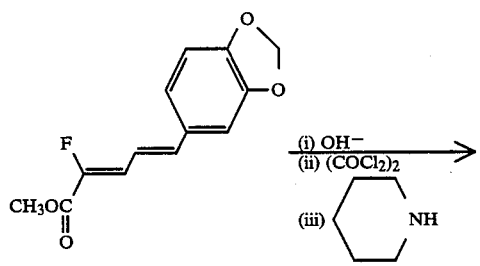

XVI

The fluorinated piperidide XVI shows the same electrophysiological effect on the central nervous system of the cockroach as the non-fluorinated insecticide piperine.

In addition, the compound XVIII below is the monofluoro analog of a known pyrethric acid derivative. The compound can be synthesized from a compound of formula V of the invention (XVII) below by the sequence shown below.

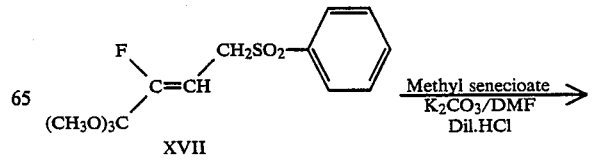

XVII

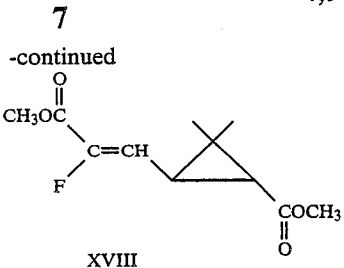

XVIII

Pyrethric acid derivatives are intermediates in the synthesis of compounds having insecticidal activity.

Other utility of the fluoro compounds and processes of the invention is in the synthesis of fluoro-Vitamin A or fluorinated prostaglandins. An important advantage of the processes of the invention is that they are stereospecific where there is the possibility of two geometric isomers about the double bond of the alkene product, yielding more than 98 percent of one isomer. This feature is especially advantageous in the synthesis of biologically active compounds, whose activity is often stereospecific.

EXAMPLES

The following examples illustrate the preparation of the compounds and the operation of the processes of the invention. A schematic outline of the illustrated reactions and compounds is shown below.

Like non-fluorinated known compounds of similar structure, compound (4) prepared using the compounds and processes of the invention will be useful as a pheromone, while compound (10) will be useful as an insecticide. Their method of use, e.g. as powders or solutions in appropriate amounts can also be according to known procedures for the prior art compounds.

In the following examples, products were identified by elemental analysis, IR spectroscopy (Perkin-Elmer 1310 infrared spectrometer), and NMR: $^1$H (Nicolet QE-300 MHz), $^{19}$F(Hitachi 90 N). (The $^{19}$F figures quoted are chemical shifts in p.p.m. from internal trichlorofluoromethane and the $^1$H figures are δ values in CDCl$_3$, internal tetramethylsilane standard), and mass spectrometry (Nermag R10-10C).

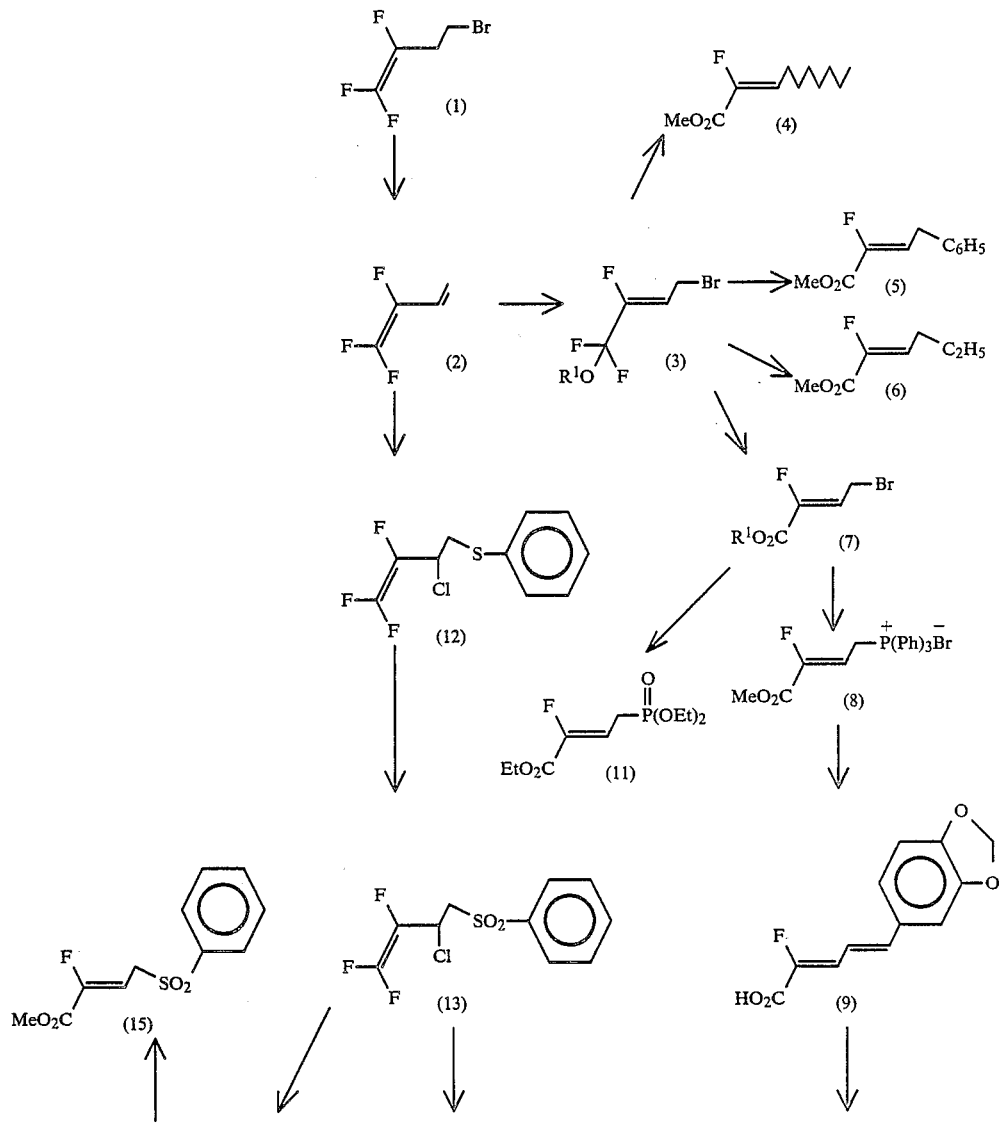

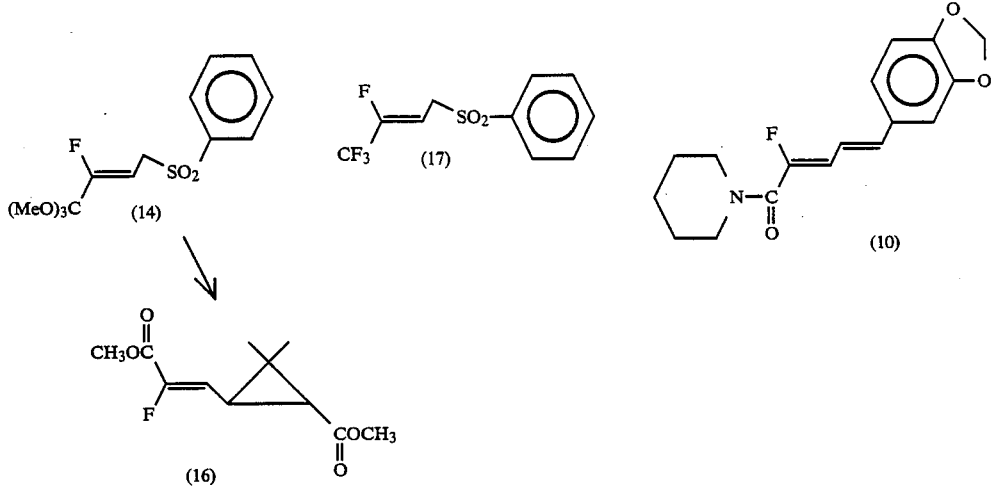

EXAMPLE 1

Example 1 illustrates the preparation of the fluorinated butadiene intermediate (compound (2) of the schematic diagram) by the process of the invention.

Synthesis of 1,1,2-Trifluoro-1,3-butadiene(2)

To a solution of 12.0 g (214 mmol) potassium hydroxide in 12.0 mL water at room temperature in a 100 mL round-bottom flask with a reflux condenser was added in one portion of a mixture of 4-bromo-1,1,2-trifluoro-1-butene (15.0 g, 79.4 mmol) and tetrabutylammonium bromide (0.50 g) in 20 mL of xylenes. A slow stream of nitrogen gas was bubbled into the reaction mixture through a glass tube extending into the solution, while the exit stream of nitrogen was passed through the vertical water-cooled reflux condenser, the calcium chloride tube and then into a trap held at −78° C. The reaction mixture was warmed to 60° C. and held there for 5 hours. The desired trifluorobutadiene was collected in the cold trap as a clear liquid (7.95 g, 93% yield) and characterized by its $^1$H-NMR (CDCl$_3$, 300 MHz): δ 5.24(1H,d,J=12Hz), 5.49(1H,d,J=18Hz), 6.20(1H,m). $^{19}$F-NMR(CDCl$_3$): $\phi$F$^3$=−15.6 ,$\phi$F$^2$=120.0, $\phi$F$^1$=103.6, J(F$^{12}$)=66.2, J(F$^{23}$)=107.5 J(F$^{13}$)=28.9 J(F$^3$H)=24.8

EXAMPLE 2

Example 2 illustrates the preparation of a masked ester compound of the invention (compound (3) of the schematic diagram, R$^1$=CH$_3$) of formula I, by the process of the invention. Only the (Z) isomer was detected in the product.

(Z)-4-Bromo-1-methoxy-1,1,2-trifluoro-2-butene (3)

To a solution of 5.30 g (49.1 mmol) 1,1,2-trifluoro-1,3-butadiene in methanol (70 mL) at 0° C. in a round-bottom 250 mL flask was added 12.50 g of potassium carbonate (anhydrous powder). The flask was equipped with a magnetic stirrer, and the stirred contents cooled to ca. −70° C. Bromine (2.50 mL, 48.4 mmol) was slowly added to the −70° C. reaction mixture over two hours, and the resulting mixture stirred for further two hours at −50° C. At this point the contents of the flask were poured into a large excess of ice-water, and the liquid extracted twice with diethyl ether. The ether layers were combined, washed once with brine, then dried over anhydrous magnesium sulfate. Evaporation of solvent gave 7.50 g (70.2%) of (Z)-4-bromo-1-methoxy-1,1,2-trifluoro-2-butene as a clear liquid which was distilled at 74° C. (40 mm Hg). H-NMR (300 MHz, CDCl): δ 3.62(3H, s), 3.98(2H, d, J=9 Hz), 5.76(1H, dt, J=9, 31 Hz). Mass spectrum: m/e=218,220 (M+). $^{19}$F-NMR (CDCl$_3$): $\phi$79.2(d, J=14.2 Hz) 126.5(dtt, J=31.0, 14.0, 2.4 Hz).

EXAMPLE 3

Example 3 illustrates the Grignard alkylation and subsequent hydrolysis process of the invention, making use of the masked ester of Example 1 as a synthetic intermediate in the preparation of compound (4) of the schematic diagram.

Synthesis of Methyl (Z)-2-Fluoro-2-decenoate (4)

To a solution of 1.0 g (4.5 mmol) 4-bromo-1-methoxy-1,1,2,-trifluoro-2-butene in 15.0 mL tetrahydrofuran at −60° C. in a 50 mL round-bottom flask was added a solution of n-hexylmagnesium bromide (2M, 5.0 mL, 10.0 mmol) in diethyl ether and followed by addition of 100 mg dilithiumcupric tetrachloride. The reaction mixture was stirred for two hours at 0° C. The contents of the flask were poured into a large excess of an aqueous ammonium chloride solution, and the liquid extracted twice with diethyl ether. The ether layers were combined, washed once with brine, then dried over anhydrous magnesium sulfate. Evaporation of solvent gave 1.20 g of 1-methoxy-1,1,2,-trifluoro-2-decene. $^1$H NMR (CDCl$_3$ 300 MHz): 0.85(3H,t), 1.23(10H,bs), 2.12(2H,m), 3.60(3H,s), 5.39(1H,dt,J=8,34Hz). Without further Purification this crude oil was transformed to the ester as follows.

To a mixture of 3 g 75% sulfuric acid and 15 mL of n-pentane at 20° C. in a round-bottom 50 mL flask was added the crude 1-methoxy-1,1,2-trifluoro-2-decene (1.2 g). The resulting mixture was stirred for 40 hours at 20° C. The reaction mixture was poured into a large excess of ice-water and the liquid extracted twice with diethyl ether. The ether layers were combined, washed with water and brine, then dried over anhydrous magnesium sulfate. Evaporation of solvent gave a yellow oil which was chromatographed on silica gel (5% ethyl acetate in hexanes) to give 0.59 g (64.5%) of methyl (Z)-2-fluoro-2-decenoate as a clear liquid: $^1$H-NMR (300 MHz, CDCl$_3$): δ 0.86(3H, t), 1.24(1OH), 2.22(2H, dq,J=2,8 Hz), 3.80(3H, s), 6.10(1H, dt, J=8, 33Hz). Mass spectrum: m/e=202 (M+). $^{19}$F-NMR (CDCl$_3$): φ 131.8(d, J=33.0).

EXAMPLE 4

Example 4 illustrates the Grignard arylation and subsequent hydrolysis process of the invention to provide the compound (5) of the schematic diagram.

Methyl (Z)-2-Fluoro-4-phenyl-2-butenoate (5)

To a solution of 1.0 g (4.5 mmol) 4-bromo-1-methoxy-1,1,2-trifluoro-2-butene in 15.0 mL tetrahydrofuran at −60° C. was added a solution of phenylmagnesium bromide (3M, 1.6 mL, 4.8 mmol) in diethyl ether and the mixture was stirred for 1 hr. at −60° C. then stirred for 12 hours at 20° C. The workup and acidic hydrolysis was done as mentioned in Example 3 to give 0.34 g (42%) of methyl (Z)-2-fluoro-4-phenyl-2-butenoate. $^1$H-NMR (300 MHz, CDCl$_3$): δ 3.58(2H, dd, J=2, 9Hz), 3.81(3H, s), 6.29(1H, dt, J=9, 31 Hz), 7.18–7.34(5H, m). Mass spectrum: m/e=194 (M+). $^{19}$F-NMR (CDCl$_3$): φ 131.3(d, J=31.1 Hz).

EXAMPLE 5

Example 5 illustrates the Grignard alkylation and subsequent hydrolysis process of the invention to provide the compound (6) of the schematic diagram.

Methyl (Z)-2-Fluoro-2-hexenoate (6)

1.0 g (4.5 mmol) of 4-bromo-1-methoxy-1,1,2-trifluoro-2-butene was treated with ethylmagnesium bromide (3M, 1.6 mL, 4.8 mmol) in diethyl ether according to the same procedure as Example 4 to give 0.29 g (48%) of methyl (Z)-2-fluoro-2-hexenoate. $^1$H-NMR (300 MHz, CDCl$_3$): δ 0.92(3H, t), 1.46(2H, q), 2.20(2H, dq, J=2, 8 Hz), 3.80(3H, a), 6.11(1H, dt, J=8, 33Hz).

EXAMPLE 6

Example 6 illustrates the preparation of a 4-halo-2-fluoro-2-alkenoate ester from the compound of Example 2 by a process of the invention, as an intermediate in the preparation of compounds according to formula III of the invention.

Methyl (Z)-4-Bromo-2-fluoro-2-butenoate (7)

To a mixture of 3.0 g 75% sulfuric acid and 15 mL n-pentane was added 1.0 g (4.6 mmol) 4-bromo-1-methoxy-1,1,2-trifluoro-2-butene at room temperature in a 50 mL round-bottom flask. The resulting mixture was stirred for 48 hours at room temperature. Excess ice water was added and the liquid extracted with diethyl ether. The ether layer was successively washed with water and brine, then dried over anhydrous magnesium sulfate. Evaporation of the solvent in vacuo gave the crude ester which was purified by chromatography on silica gel to give 0.62 g (68.9%) of methyl (Z)-4-bromo-2-fluoro-2-butenoate. Analytical sample distilled a 90°–92° C. (18 mm Hg). $^1$H-NMR (300 MHz, CDCl$_3$) δ 3.84(3H, s), 4.40(2H, dd, J=2.5, 9 Hz), 6.35(1H, dt, J=9, 30 Hz). $^{19}$F-NMR (CDCl$_3$): φ 122.5(d, J=30.2 Hz).

EXAMPLE 7

Example 7 illustrates the preparation of a triphenylphosphonium compound according to formula III of the invention, compound (8) of the schematic diagram.

(Z)-3-Fluoro-3-methoxycarbonyl-2-propenyltriphenylphosphonium Bromide (8)

2.0 g (7.6 mmol) triphenylphosphine was added to a solution of 1.50 g (7.6 mmol) methyl 4-bromo-2-fluoro-2-butenoate in 20 mL of toluene at room temperature in a 50 mL round-bottom flask. The flask was equipped with a reflux condenser and the mixture was stirred for 10 hours at 60° C. The contents of the flask were filtered and the white precipitate was washed with excess toluene. The precipitate was purified by recrystallization from ethyl acetate and chloroform (1:1) to give 3.1 g (88.6%) of the phosphonium salt as a white powder, m.p. 145°–147° C. (decomp.). Anal.: Calcd. for C$_{23}$H$_{21}$BrFO$_2$P: C, 60.12; H, 4.61; Br. 17.41. Found: C. 59.84; H. 4.97; Br. 17.03.

EXAMPLE 8

The triphenylphosphonium compound of the invention of Example 7 is converted to the 2-fluoro analog of the known insecticide piperine (a compound of formula VI of the invention) by the reactions described in Examples 8 and 9.

(2Z,4E)-2-Fluoro-5-(3,4-methylenedioxyphenyl)-penta-2,4-dienoic Acid (9)

Sodium hydride (0.13 g. 2.7 mmol, 50% dispersion in mineral oil) was added to a mixture of 1.21 g (2.6 mmol) (Z)-3-fluoro-3-methoxycarbonyl-2-propenyl triphenylphosphonium bromide in 20 mL of tetrahydrofuran at 0° C. in a 50 mL round-bottom flask under a nitrogen atmosphere. The reaction mixture was stirred for three hours at 20° C. Subsequently, 0.39 g (2.6 mmol) of piperonal was added to the mixture at 20° C. in one portion and the resulting mixture stirred further for twelve hours at 20° C. Then 30 mL hexanes was added to the reaction, and the whole mixture was filtered. The filtrate was evaporated in vacuo to give crude methyl 2-fluoro-5-(3,4-methylenedioxyphenyl)-penta-2,4-dienoate (0.8 g). This was revealed to be a 1:1 mixture of 4E and 4Z isomers according to the proton NMR. $^1$H-NMR of the product (E,Z mixture): H$_2$ and H$_1$ protons of (2Z, 4Z)-isomer appeared at δ 6.46 as a triplet (J=10 Hz) and at 7.06 as a double doublet (J=12, 32Hz), respectively. Without purification, the crude material was dissolved in 5 mL tetrahydrofuran. To this solution was added 66 mg (0.6 mmol) thiophenol and 28 mg (0.58 mmol) sodium hydride (50% dispersion in mineral oil) at 20° C. The resulting mixture was stirred for twelve hours at 20° C. The contents of the flask were poured into 10 mL of cooled 5% aqueous hydrochloric acid, and the liquid extracted twice with diethyl ether. The ether layers were combined, washed successively with 5% sodium bicarbonate solution and brine, then dried over anhydrous magnesium sulfate. Evaporation of solvent gave 0.7 g of a crude (2Z,4E)-ester. This was dissolved in 5.2 mL methanolic potassium hydroxide at 20° C. The solution was left standing for 30 hours at 20° C. At this point the contents of the flask were poured into 10 mL 5% aqueous hydrochloric acid and the mixture extracted twice with ethyl acetate. The organic layers were combined, washed once with brine, then dried over anhydrous magnesium sulfate. Evaporation of the solvent gave the crude (0.42 g) (2Z,4E)-acid. Recrystallization from 30% ethyl acetate in n-hexane gave 0.25 g 40.8% yield from (Z)-3-fluoro-3-methoxycarbonyl-2-propenyltriphenylphosphonium bromide) (2Z,4E)-2-fluoro-5-(3,4-methylenedioxyphenyl)-penta- 2,4-dienoic acid as white crystals, mp 225° C. (decomp.): $^1$H-NMR (300 MHz,CDCl$_3$): 5.80(2H, s), 6.52(dd, J=12, 30 Hz). Anal.: Calcd. for C$_{12}$H$_9$FO$_4$: C, 61.00; H, 3.84. Found: C, 60.95; H, 3.76.

EXAMPLE 9

(2Z,4E)-2-Fluoro-5-(3,4-methylenedioxyphenyl)-penta-2,4-dienoic Acid Piperidide (10)

Oxalyl chloride (0.5 mL, 5.7 mmol) was added to a solution of 80.5 mg (0.34 mmol) (2Z,4E)-2-fluoro-5-(3,4-methylenedioxyphenyl)-penta-2,4-dienoic acid in 1 mL of tetrahydrofuran in a round-bottom 10 mL flask at 20° C. The resultant solution was stirred for one hour at 50° C. Evaporation of solvent gave the crude acid chloride. To a solution of this acid chloride in 1 mL benzene was added 0.3 mL (3.0 mmol) piperidine at 20° C. The mixture was stirred one hour at 20° C. the reaction mixture was poured into 2 mL ice-cooled 5% aqueous hydrochloric acid, and the liquid extracted once with ethyl acetate. The organic layer was washed successively with 5% aqueous sodium bicarbonate solution and brine, then dried over anhydrous magnesium sulfate. Evaporation of solvent followed by chromatography on silica gel (elution with 30% ethyl acetate in n-hexane) gave a white solid. This was recrystallized from 30% ethyl acetate in hexanes to give 50.0 mg (49%) of the piperidide of (2Z,4E)-2-fluoro-5-(3,4-methylenedioxyphenyl)-penta-2,4-dienoic acid as white crystals, mp 97.5°-98.0° C. $^1$H-NMR (300 MHz, CDCl$_3$): δ 1.62(6H, m), 3.53(4H, m), 5.95(2H, s), 6.39(1H, dd, J=10, 33 Hz), 6.62(1H, d,J=16 Hz), 6.75(1H, d, J=8 Hz), 6.84(1H, dd, J=10, 16 Hz), 6.87(1H, d, J=8,Hz), 6.98(1H, s). Mass spectrum: m/e=303 (M+). Anal.: Calcd. for C$_{17}$H$_{18}$FO$_3$N: C, 67.29; H, 5.99; N, 4.62. Found: C, 67.22; H, 6.12; N, 4.64.

This fluorinated piperidide showed the same electrophysiological effect on the central nervous system of the cockroach as the non-fluorinated analog, the known insecticide piperine.

EXAMPLE 10

Example 10 illustrates the preparation of a phosphonate of formula III of the invention using a process of the invention.

Ethyl (Z)-2-Fluoro-4-(diethylphosphono)-2-butenoate (11)

2.0 g (12.0 mmol) Triethylphosphite was added to 2.5 g (11.8 mmol) ethyl 4-bromo-2-fluoro-2-butenoate (prepared analogously to compound (7)) in a 10 ml round-bottom flask. The flask was heated for 2 hours at 120° C. to remove ethyl bromide. The content of the flask was distilled to give 2.5 g (79%) of the phosphonate as a clear liquid, b.p. 125°-133° C. (0.14 mmHg). $^1$H-NMR (90 MHZ, CDCl$_3$): δ 1.32 (9 H, t), 2.75 (2H, ddd, J=2, 9, 23 Hz), 4.2 (6H, m), 6.15 (1H, ddt, J=7, 9, 31).

EXAMPLE 11

Example 11 illustrates the preparation of a compound of the invention of formula II using a process of the invention.

3-Chloro-4-phenylthio-1,1,2-trifluoro-1-butene (12)

To a solution of 1,1,2-trifluoro-1,3-butadiene (8.0 g. 74 mmol) and calcium carbonate (50 mg) in 85 mL of dichloromethane at −40° C. in a round-bottom 250 mL flask was added a solution of phenylsulfenyl chloride (7.1 g, 49 mmol) in 20 mL of dichloromethane over 2 hours. The reaction mixture was left to stand overnight at room temperature and poured into ice water. The organic layer was washed with aqueous 5% sodium metabisulfite solution and brine, then dried over anhydrous magnesium sulfate. Evaporation of solvent followed by distillation gave 12.1 g (97.5%) of 3-chloro-4-phenylthio-1,1,2-trifluoro-1-butene as a light yellow oil, bp 84°-86° C. (1.0 mm Hg). $^1$H-NMR (300 MHz, CDCl$_3$): δ 3.39(2H, d, J=8 Hz), 4.58(1H, ttd, J=1.5, 8, 33 Hz), 7.2-7.4(5H, phenyl protons). Mass spectrum: m/e=252,254 (M+). $^{19}$F-NMR (300 MHz, CDCl$_3$): φ F$^3$=−11.8, F$^2$=116.7, F$^1$=99.3. J(F$^{12}$)=64.5, J(F$^{23}$)=111.2, J(F$^{13}$)=33.0, J(F$^3$H)=26.4.

EXAMPLE 12

Example 12 illustrates the preparation of a sulfonyl compound of formula II of the invention from the thio compound of Example 11.

3-Chloro-4-phenylsulfonyl-1,1,2-trifluoro-1-butene (13)

To a solution of 7.0 g (27.7 mmol) 3-chloro-4-phenylthio-1,1,2-trifluoro-1-butene in 100 mL dichloromethane at 0° C. in a 250 mL round-bottom flask was added a solution of 15.0 g (87 mmol) 3-chloroperoxybenzoic acid in 50 mL dichloromethane. The mixture was further stirred for three hours at room temperature. At this point the contents of the flask were washed with 5% aqueous sodium bisulfite solution, saturated sodium bicarbonate solution and brine, and dried over anhydrous magnesium sulfate. Evaporation of solvent gave a yellow crystalline product, which was purified by recrystallization from n-hexane and ethyl acetate (3:1) to obtain 7.45 g (94.7%) 3-chloro-4-phenylsulfonyl-1,1,2-trifluoro-1-butene as white crystals, mp 45°-47° C. $^1$H-NMR (300 MHz, CDCl$_3$): δ 3.63(1H, ddd, J=1.5, 5, 14 Hz), 3.87(1H, dd, J=10, 14 Hz), 5.10(1H, dm, J=27 Hz), 7.6-8.0(5H, phenyl protons). Mass spectrum: m/e=284 (M+). $^{19}$F-NMR (CDCl$_3$): φ F$^1$=97.5, F$^2$=112.8, F$^3$=−13.9, J(F$^{12}$)=60.1, J(F$^{23}$)=113.8, J(F$^{13}$)=33.1, J(F$^3$H)=24.8. Anal.: Calcd. for C$_{10}$H$_8$ClF$_3$SO$_2$: C, 42.17; H, 2.83; S, 11.27; Cl, 12.46. Found: C, 42.75; H, 2.94; S, 11.18; Cl, 12.62.

EXAMPLE 13

Example 13 illustrates the preparation of an orthoester of formula V of the invention from the compound of Example 12.

(Z)-3-Fluoro-4,4,4-trimethoxy-2-butenyl Phenylsulfone (14)

Potassium carbonate (6.0 g, 43.5 mmol) was added to a solution of 3.0 g (10.5 mmol) 3-chloro-4-phenylsulfonyl-1,1,2-trifluoro-1-butene in 30 mL methanol at room temperature in a 100 mL round-bottom flask. The resulting mixture was stirred for 12 hours at room temperature. The reaction was diluted with 100 mL diethyl ether. The contents of the flask were filtered and the white solid was washed with excess diethyl ether. The ether solution was evaporated in vacuo to give 3.1 g (95%) of the crude 3-fluoro-4,4,4-trimethoxy-2-butenyl phenylsulfone as an oil. $^1$H-NMR (300 MHz, CDCl$_3$): δ 3.10(9H, s), 3.98(2H, d, J=9 Hz), 5.50(1H, dt, J=9, 33 Hz), 7.50-7.90(phenyl protons 5H). $^{19}$F-NMR (CDCl$_3$): φ 120.5(d, J=31.1). Anal.: Calcd. for C$_{13}$H$_{17}$FO$_5$S: C, 51.28; H, 5.63; S, 10.54. Found: C, 51.29; H, 5.61; S, 10.84.

EXAMPLE 14

Example 14 illustrates the preparation of a compound of formula III of the invention from the compound of Example 12.

Methyl (Z)-2-Fluoro-4-phenylsulfonyl-2-butenoate (15)

Potassium carbonate (6.0 g, 43.5 mmol) was added to a solution of 3.0 g (10.5 mmol) 3-chloro-4-phenylsulfonyl-1,1,2-trifluoro-1-butene in 30 mL methanol at room temperature in a 100 mL round-bottom flask. The resulting mixture was stirred for 12 hours at room temperature. After removal of solvent in vacuo, the residue was partitioned between 50 mL diethyl ether and 50 mL 10% aqueous hydrochloric acid. The whole mixture was stirred for one hour at room temperature. The ether layer was washed once with brine, then dried over anhydrous magnesium sulfate. Evaporation of solvent gave a crystalline product, which was purified by recrystallization from 30% ethyl acetate in hexanes to give 2.50 g (93.9%) methyl 2-fluoro-4-phenylsulfonyl-2butenoate as pale yellow crystals, mp 104.0°–105.0° C. $^1$H-NMR (300 MHz, CDCl$_3$): δ 3.82(3H, s), 4.05(2H, dd, J=28 Hz), 6.17(1H, dt, J=8, 30 Hz), 7.55–7.9(phenyl protons 5H). Mass spectrum: m/e=258 (M+). $^{19}$F-NMR (CDCl$_3$): φ 121.4(d, J=31.0). Anal.: Calcd. for C$_{11}$H$_{11}$FO$_4$S: C, 51.16; H, 4.26. Found: C, 51.02; H, 4.37.

EXAMPLE 15

Example 15 illustrates the preparation of the monofluoro analog of a known pyrethric acid derivative from the compound of the invention of Example 13.

Methyl (Z)-cis, trans-2,2-Dimethyl-3-(2-fluoro-2-methoxycarbonylvinyl) cyclopropane Carboxylate (16)

To a solution of 589 mg (1.94 mmol) (Z)-3-fluoro-4,4,4-trimethoxy-2-butenyl phenylsulfone and 486 mg (4.26 mmol) methyl senecioate in dimethylformamide (4 mL) at 20° C. in a pear-shaped 50 mL flask was added 280 mg (5.19 mmol) of sodium methoxide. The flask was equipped with a magnetic stirrer and stirred for 48 hours under N$_2$ atmosphere. The reaction mixture was poured into 5% aqueous hydrochloric acid and the mixture extracted with diethyl ether. Evaporation of solvent yielded crude liquid which was diluted with 10 mL methanol. p-Toluenesulfonic acid (10 mg) was added to the solution and the resulting solution was stirred for 1 hour. The reaction mixture was diluted with excess 5% sodium bicarbonate solution and diethyl ether. The ether layer was washed with brine, then dried over anhydrous magnesium sulfate. Evaporation of the solvent in vacuo gave the crude diester which was purified by chromatography on silica gel to give 178 mg (40.0%) of methyl (Z)-cis, trans-2,2-dimethyl-3-(2-fluoro-2-methoxycarbonylvinyl)cyclopropanecarboxylate (trans:cis=85:15). $^1$H-NMR (300 MHz, CDCl$_3$): δ 1.19, 1.26 (trans gem-dimethyl), 1.23 cis gem-dimethyl), 1.73(trans isomer, d, J=5.0 Hz), 2.39(trans isomer, dd, J=5, 10 Hz), 1.94(cis isomer, d, J=9 Hz), 2.10(cis isomer, dd, J=9, 10 Hz), 5.84(trans isomer, dd, J=10, 32), 6.59(cis isomer, dd, J=10, 31 Hz). Mass spectrum: m/e=231 (M+1). $^{19}$F-NMR (CDCl$_3$): φ 131.6(d, J=32.0, trans), 132.7(d, J=31.1, cis). Anal.: Calcd. for C$_{11}$H$_{11}$FO$_4$: C, 57.36; H, 6.57. Found: C, 57.25; H, 6.61.

EXAMPLE 16

Example 16 illustrates the preparation of a compound of the invention of formula IV from the compound of the invention of Example 12.

(Z)-3,4,4,4-Tetrafluoro-2-butenyl Phenylsulfone (17)

Potassium fluoride (239 mg, 3.1 mmol, Aldrich Gold Label) was added to a solution of 237 mg (0.83 mmol) 3-chloro-4-phenylsulfonyl-1,1,2-trifluoro-1-butene in 2 mL dry dimethylformamide in a 20 mL round-bottom flask. The mixture was stirred for 15 hours at room temperature. At this point the contents of the flask were poured into ice water, and the mixture extracted with diethyl ether. The ether layer was washed once with brine, then dried over anhydrous magnesium sulfate. Evaporation of solvent yielded crude solid, which was purified by recrystallization from 30% ethyl acetate in hexanes to give 184 mg (82.5%) of 3,4,4,4-tetrafluoro-2-butenyl phenylsulfone as white crystals, mp 83.0°–84.0° C. $^1$H-NMR (300 MHz, CDCl$_3$): δ 3.94(2H, d, J=9 Hz), 5.73(1H, dt, J=8.31 Hz), 7.6–7.9(5H, phenyl protons). Mass spectrum: m/e=268 (M+). $^{19}$F-NMR (CDCl$_3$): φ 72.7(d, J(CF$_3$-F)=10.3) 127.3(dqt, J(F-H trans)=31.0, J(F-CF$_3$)=10.3). Anal.: Calcd. for C$_{10}$H$_8$F$_4$SO$_2$: C, 44.76; H, 3.01. Found: C, 44.58; H, 3.02.

Variations and modifications of the above-described invention may suggest themselves to those skilled in the art. Accordingly, the above description should not be taken in a limiting sense.

We claim:

1. Z-isomers of fluorinated alkene compounds of the formula

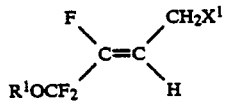

wherein R$^1$ is C$_1$–C$_4$ alkyl; X$^1$ is C$_1$–C$_8$ alkyl, C$_2$–C$_8$ alkenyl, C$_2$–C$_8$ alkynyl, aryl, aralkyl chlorine, or bromine.

2. The compound (Z)-4-bromo-1-methoxy-1,1,2-trifluro-2-butene.

3. A process for preparing a compound of the formula

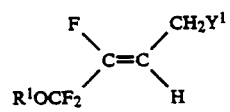

wherein Y$^1$ is chlorine or bromine and R$^1$ is C$_1$–C$_4$ alkyl which comprises causing a diene of the formula

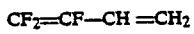

to react with a source of positive chlorine or bromine in a lower alkanol solvent.

4. A process according to claim 3 wherein the reaction is carried out in the presence of a weak base.

* * * * *